United States Patent [19]

Nakagawa et al.

[11] Patent Number: 5,474,963
[45] Date of Patent: Dec. 12, 1995

[54] CATALYST FOR DIMERIZING α-OLEFIN MONOMER

[75] Inventors: Kanji Nakagawa; Hiroshi Shimazaki; Makoto Matsuo; Koji Miyauchi; Toshikazu Machida, all of Ichihara, Japan

[73] Assignee: Ube Industries, Ltd., Yamaguchi, Japan

[21] Appl. No.: 223,443

[22] Filed: Apr. 5, 1994

[30] Foreign Application Priority Data

| Apr. 9, 1993 | [JP] | Japan | 5-083303 |
| Nov. 19, 1993 | [JP] | Japan | 5-290862 |
| Dec. 17, 1993 | [JP] | Japan | 5-318381 |
| Jan. 25, 1994 | [JP] | Japan | 6-006582 |

[51] Int. Cl.$^6$ .............. B01J 21/18; B01J 23/02; B01J 23/48
[52] U.S. Cl. .............. 502/184; 502/174; 502/180; 502/181; 502/182; 502/224; 502/300
[58] Field of Search .............. 502/174, 180, 502/181, 182, 184, 224, 300

[56] References Cited

U.S. PATENT DOCUMENTS

| 4,296,265 | 10/1981 | Ohsaka et al. . | |
| 4,520,126 | 5/1985 | Kawamoto et al. . | |
| 4,595,787 | 6/1986 | Drake et al. . | |
| 4,727,213 | 2/1988 | Drake et al. . | |
| 4,835,330 | 5/1989 | Drake et al. . | |
| 4,908,198 | 3/1990 | Weinberg | 502/181 |
| 4,950,632 | 8/1990 | Drake et al. . | |
| 5,081,094 | 1/1992 | Drake et al. . | |
| 5,202,298 | 4/1993 | Schubert et al. | 502/174 |

FOREIGN PATENT DOCUMENTS

| 55-14533 | 11/1980 | Japan . |
| 58-114739 | 7/1983 | Japan . |
| 58-114738 | 7/1983 | Japan . |
| 58-114736 | 7/1983 | Japan . |
| 58-114737 | 7/1983 | Japan . |
| 342043 | 2/1991 | Japan . |

*Primary Examiner*—Asok Pal
*Assistant Examiner*—E. D. Irzinski
*Attorney, Agent, or Firm*—Burgess, Ryan & Wayne

[57] ABSTRACT

A catalyst for dimerizing a lower α-olefin monomer with an enhanced selectivity comprises a carrier comprising at least one anhydrous potassium compound, preferably a mixture of potassium fluoride with potassium carbonate, and a carbon material; and a catalytic component carried on the carrier and comprising an alkali metal, preferably sodium metal, the catalyst preferably being compression molded into grains.

9 Claims, No Drawings

CATALYST FOR DIMERIZING α-OLEFIN MONOMER

BACKGROUND OF THE INVENTION

1. Field of the Invention

The present invention relates to a catalyst for dimerizing at least one lower α-olefin monomer.

More particularly, the present invention relates to a catalyst for dimerizing a lower α-olefin monomer or for codimerizing two different lower α-olefin monomers, which catalyst has an enhanced catalytic activity and is useful for producing an α-olefin dimer with a high selectivity.

2. Description of Related Art

Japanese Examined Patent Publication (Kokoku) No. 42-22474 discloses a method of producing 4-methylpentene-1 by dimerizing propylene by employing a catalyst in which sodium metal is carried on a carrier consisting of a potassium compound. In this Japanese publication, as an example of the potassium compounds, potassium halides are indicated in addition to potassium carbonate. This Japanese publication, however, does not concretely teach or suggest the specific type of the potassium halides and the specific effect thereof.

Also, Japanese Examined Patent Publication (Kokoku) No. 63-25,816 indicates, as a potassium compound useful for the catalyst, potassium chloride and potassium bromide in addition to potassium carbonate. This publication, however, does not indicate a specific effect of the potassium chloride and potassium bromide.

The above-mentioned publications are completely silent as to the utilization of potassium fluoride as a component of the carrier of the α-olefin-dimerizing catalyst.

U.S. Pat. No. 4,950,632 discloses a catalyst containing, as a carrier, a mixture of potassium carbonate with potassium nitrate. Also, U.S. Pat. No. 5,081,094 discloses a catalyst containing, as a carrier, a mixture of potassium carbonate with potassium hydrogencarbonate. However, when these catalysts are employed for the dimerization of propylene, even where the selectivity of the aimed 4-methylpentene-1 is about 90%, the conversion of propylene is very low, namely, 10% to 25%. Also, potassium nitrate is disadvantageous in a high risk of explosion thereof.

Japanese Examined Patent Publication (Kokoku) No. 59-40,504 discloses a catalyst in which a mixture of sodium with potassium is carried on a carrier comprising potassium carbonate mixed with graphite. This catalyst is also disadvantageous in that the catalytic activity the catalyst is poor and/or the selectivity of 4-methylpentene-1 is not high enough for practical use.

In preparation of a homodimer of a lower α-olefin monomer or a codimer of two different types of α-olefin monomers, many types of catalysts in which a alkali metal is carried on a carrier are known. When the catalyst is employed in an industrial scale, it is advantageous to employ a compression-molded carrier in the form of grains.

Nevertheless, it is known that the conventional compression-molded carrier grains cause the resultant catalyst to be unsatisfactory in both the catalytic activity and the selectivity or in the selectivity even if the catalytic activity is satisfactory. Therefore, almost all of the conventional catalysts including the compression-molded carrier grains are not practically useful.

In the industrial preparation of the α-olefin dimers, the selectivity of the α-olefin monomer to the aimed dimer is most important and thus must be as high as possible. Accordingly, a development of a new catalyst useful for producing the α-olefin dimer with a high selectivity is strongly demanded.

As the compression-molded grain type catalyst, Japanese Examined Patent Publications (Kokoku) No. 59-40,503, No. 59-40,504, No. 59-40,506 and Japanese Unexamined Patent Publication (Kokai) No. 3-42,043 disclose catalysts in which metallic sodium is carried on compression-molded grain type carrier comprising a mixture of anhydrous potassium carbonate and carbon. Also, Japanese Examined Patent Publication (Kokoku) No. 59-40,505 discloses a catalyst comprising a compression-molded grain type carrier comprising anhydrous potassium carbonate and carbon, and a mixture of metallic sodium with potassium carbonate and carbon carried on the carrier.

When the above-mentioned catalyst is employed for the dimerization of propylene, the aimed compound, namely 4-methylpentene-1 is produced with a relatively high selectivity of 90 to 93%. This selectivity is, however, still unsatisfactory.

Japanese Unexamined Patent Publication (Kokai) No. 62-38,240 discloses a catalyst produced by oxidize-treating pellets consisting of potassium carbonate and carbon and then carrying metallic potassium on the pellets. U.S. Pat. No. 4,727,213 discloses a catalyst in which metallic potassium is carried on pellets consisting of potassium carbonate, calcium aluminate and carbon. U.S. Pat. No. 4,835,330 discloses a catalyst comprising a glass powder and metallic potassium carried on pellets comprising potassium carbonate and carbon. Those catalysts are, however, unsatisfactory because when used for dimerizing propylene, the selectivity of the resultant 4-methylpentene-1 is low, namely 90% at the highest.

In the dimerization of an α-olefin monomer, for example, propylene, the resultant reaction product contains isomers of 4-methylpentene-1, for example, 4-methylpentene-2, 2-methylpentene-2 and hexene, as by-products. Among the isomers, 4-methylpentene-2 has a boiling temperature very close to that of 4-methylpentene-1 and thus is difficult to separate it from 4-methylpentene-1 by a distillation procedure for isolating 4-methylpentene-1. This difficulty causes the resultant 4-methylpentene-1 product to exhibit a reduced degree of purity. Accordingly, there is a strong demand of providing a new catalyst effectively prevent or restrict the production of 4-methylpentene-2.

The boiling points of isomers of propylene dimers are as follows.

| Compound | Melting point |
| --- | --- |
| 4-methylpentene-1 | 53.9° C. |
| cis-4-methylpentene-2 | 56.3° C. |
| trans-4-methylpentene-2 | 58.6° C. |
| 2-methylpentene-1 | 60.7° C. |
| hexene-1 | 63.5° C. |
| cis-hexene-3 | 66.4° C. |
| trans-hexene-3 | 67.1° C. |
| 2-methylpentene-2 | 67.3° C. |
| trans-hexene-2 | 67.9° C. |
| cis-hexene-2 | 68.8° C. |

SUMMARY OF THE INVENTION

An object of the present invention is to provide a catalyst for dimerizing at least one lower α-olefin monomer, having a high catalytic activity and being capable of enhancing a selectivity to the aimed dimer, and a method of dimerizing the α-olefin monomer with a high selectivity to the aimed dimer.

Another object of the present invention is to provide a catalyst for dimerizing at least one lower α-olefin monomer, capable of effectively preventing production of a by-product which is difficult to separate from the aimed dimer, and a method of dimerizing at least one lower α-olefin, while preventing production of a by-product which is difficult to separate from the aimed dimer.

The above-mentioned objects can be attained by the catalyst and method of the present invention.

The catalyst of the present invention for dimerizing at least one lower α-olefin, comprises a carrier comprising a mixture of a first moiety which comprises at least one anhydrous potassium compound and a second moiety which comprises at least one carbon material; and a catalytic component carried on the carrier and comprising at least one alkali metal, the first moiety of the carrier comprising at least anhydrous potassium fluoride.

In the method of the present invention, the dimerization of at least one lower α-olefin monomer is carried out in the presence of the catalyst as mentioned above.

In the catalyst of the present invention, the first moiety of the carrier preferably comprises a mixture of anhydrous potassium fluoride with anhydrous potassium carbonate.

Also, it is preferable that the carrier of the catalyst of the present invention be in the form of compression-molded grains.

Further, it is preferable that the compression-molded grains of the catalyst carrier have a specific surface area of 0.25 m$^2$/g or more determined by the BET method.

DESCRIPTION OF THE PREFERRED EMBODIMENTS

The catalyst of the present invention comprises a carrier and a catalytic component carried on the carrier. The carrier comprises a mixture of a first moiety comprising at least one anhydrous potassium compound which must include at least anhydrous potassium fluoride, with a second moiety comprising at least one carbon material. Also, the catalytic component comprises at least one alkali metal.

The first moiety of the catalyst carrier comprises potassium fluoride alone, or a mixture of potassium fluoride with at least one potassium compound other than potassium fluoride, preferably a mixture of potassium fluoride with potassium carbonate.

In the first moiety of the catalyst carrier, the presence of potassium fluoride enhances the catalytic activity of the resultant catalyst for the dimerization of the lower α-olefin. For this purpose, the potassium fluoride is preferably present in an amount of at least 5% by weight based on the total weight of the first moiety.

When the first moiety comprises a mixture of potassium fluoride with potassium carbonate, the mixing ratio thereof is not limited to a specific range of the mixing ratio.

In the first moiety, however, preferably the potassium fluoride is present in an amount of 10 to 80%, more preferably 20 to 70% by weight and the potassium carbonate is present in an amount of 90 to 20% more preferably 80 to 30% by weight based on the total weight of potassium fluoride and potassium carbonate. When potassium fluoride and potassium carbonate are mixed with each other in the above-mentioned mixing weight ratio the resultant carrier effectively causes the aimed dimer to be produced with a significantly enhanced selectivity. Also, in this case, the resultant carrier exhibits an enhanced affinity to and supporting property for the alkali metals.

In the first moiety of the catalyst carrier, potassium fluoride or the mixture of potassium fluoride with potassium carbonate may be mixed with at least one member selected from potassium halides, for example, potassium chloride, potassium bromide and potassium iodide, potassium sulfate, potassium nitrate, potassium silicate and potassium silicofluoride, in a small amount, for example, 10% by weight or less, based on the total weight of the first moiety. The first moiety may be in the form of fine particles, grains or pellets.

In the catalyst carrier, the second moiety comprises at least one carbon material. The carbon material is preferably selected from the group consisting of activated carbon, graphite and carbon black. The second moiety may consist of one, two or more of the above-mentioned carbon materials. Preferably, the second moiety comprises graphite. The second moiety is not limited to ones having a specific form and is preferably in the form of a fine powder.

The amount of the second moiety is not limited to a specific range thereof. Preferably, the second moiety is contained in an amount of 0.2 to 3.0% by weight based on the total weight of the catalyst.

If the amount of the second moiety is less than 0.2% or more than 3.0%, the resultant catalyst sometimes exhibits an unsatisfactory catalytic activity.

The catalyst of the present invention may be in the form of a powder, grains or pellets. Preferably, the catalyst of the present invention is in the form of compression-molded grains. Also, the compression molded grains of the catalyst of the present invention preferably have a specific surface area of 0.25 m$^2$/g or more, more preferably 0.3 to 30 m$^2$/g.

It is known that the anhydrous potassium compounds, for example, anhydrous potassium fluoride and potassium carbonate, are in the form of a fine particles having a low specific surface area. When the anhydrous potassium compound containing first moiety is compression-molded together with the second moiety, the resultant grains exhibit a reduced specific surface area due to the compression-densification applied thereto. This reduction in the specific surface area causes the resultant catalyst to exhibit a reduced selectivity to the aimed dimer. In the present invention, the compression-molding for the catalyst grains is carried out preferably to an extent that the resultant compression-molded catalyst carrier exhibits a specific surface area of 0.25 m$^2$/g or more, more preferably 0.3 to 3.0 m$^2$/g.

When the specific surface area of the compression-molded carrier is less than 0.25 m$^2$/g, the resultant catalyst causes the aimed dimer to be produced in a reduced selectivity thereto. Also, if the specific surface area is significantly smaller than 0.25 m$^2$/g, the resultant carrier exhibits a reduced absorption of the alkali metal, namely the catalytic component, and thus the resultant catalyst contain the alkali metal in an unsatisfactory amount. Also, non-absorbed fraction of the alkali metal adheres on the catalyst grain surfaces and thus the resultant catalyst grains exhibit a high stickiness and adhere to each other so as to make them useless.

In the catalyst of the present invention, the catalytic component carried on the carrier comprises at least one alkali metal. The alkali metal is selected from sodium and potassium metals and mixtures thereof.

Generally, the sodium metal exhibits a catalytic activity lower than that of the potassium metal. However, when the sodium metal is brought into contact with an anhydrous potassium compound, for example, potassium fluoride or potassium carbonate, while heated, an exchange reaction easily occurs between the sodium metal and the anhydrous potassium compound so that the sodium metal is converted to a corresponding anhydrous sodium compound, for example, sodium fluoride or sodium carbonate, and the anhydrous potassium compound is converted to potassium metal. Accordingly, in the catalyst of the present invention, the catalytic component may consist of the sodium metal alone. In the method of the present invention, when the sodium metal is used as an alkali component to be carried on the carrier, the resultant catalyst exhibits an excellent selectivity enhancing effect for the aimed dimer.

In the catalyst of the present invention, the amount of the catalytic component is not restricted to a specific range thereof. Preferably, the catalytic component is present in an amount of 1 to 10%, more preferably 1.5 to 6%, by weight based on the total weight of the catalyst.

Generally, an increase in the content of the catalytic component contained in the catalyst causes the production rate of the aimed α-olefin dimer per unit weight of the catalyst to increase, and this results in an enhanced industrial benefit. However, if the content of the catalytic component comprising at least one alkali metal is too high, sometimes heat removal becomes difficult and/or the resultant catalyst exhibit a reduced selectivity-enhancing effect for the aimed α-olefin dimer.

The catalyst carrier is prepared by mixing the first moiety material and the second moiety material both in the form of a powder, or by compression-molding the mixture by using a pellet forming machine, a compression molding machine or a pelletizer to form compression-molded grains.

The first moiety material comprises at least one anhydrous potassium compound dried, at a temperature of 100° C. or more, preferably 200° C. or more, more preferably 250° C. to 500° C.

The first moiety material, before mixing with the second moiety material and compression-molding, preferably has a bulk density of 0.6 to 1.2 g/ml. If the bulk density is less than 0.6 g/ml, the flowing property of the first moiety material is poor and thus the compression-molding procedure becomes difficult. Also, if the bulk density is more than 1.2 g/ml, although the compression molding procedure can be carried out easily, the resultant compression-molded carrier grains become too dense and have an undesirably low specific surface area.

When the first moiety comprises a mixture of anhydrous potassium fluoride and potassium carbonate, they may be directly mixed to each other, or mixed after crushing and/or granulating with each other. Otherwise, they may be crushed after mixing.

The compression-molded carrier grains are not restricted to ones having a specific form and specific dimensions. Usually, the carrier grains are preferably in the form of a circular cylinder or column, a pellet or a sphere, and have a size of 0.5 mm or more, more preferably 1 to 10 mm. The mechanical strength of the compression-molded carrier grains is not limited to a specific range thereof. Preferably, the compression-molded carrier grains have a crushing strength of 1.5 to 20 kg in a radius direction of the grains.

Before applying the catalytic component to the carrier, the compression-molded carrier grains must be dried.

For this purpose, the carrier is dried at a temperature of 50° C. to 200° C. under a reduced pressure and/or calcined at a temperature of 200° C. to 600° C. under the ambient atmospheric pressure.

When the catalytic component is applied to the carrier, the dried and/or calcined carrier is mixed with the catalytic component at a temperature equal to or higher than the melting temperature of the catalytic component, preferably, of 200° C. to 450° C., in an inert gas atmosphere, while stirring. Where sodium metal is used as a material for the catalytic component, during the above-mentioned mixing procedure, a portion of the potassium compound in the carrier is converted to potassium metal and the sodium metal is converted to a corresponding sodium compound by an exchange reaction.

The crushing strength of the carrier is not largely reduced by the mixing procedure, and thus the resultant catalyst has a satisfactory mechanical strength for practical use.

Where a carrier in the state of a powder is used, the catalyst is prepared by the following procedures.

(1) The first moiety material comprising at least one anhydrous potassium compound, the second moiety material comprising at least one carbon material and the catalytic component material comprising at least one alkali metal are mixed altogether.

(2) The second moiety material and the catalytic component material are separately mixed with the first moiety material. In this procedure, the catalytic component material is preferably mixed in a final stage.

In another catalyst-preparing procedure, the first moiety material is molded to form grains or pellets, and the second moiety material and the catalytic component material are mixed to the first moiety grains. In this case, the catalytic component material is preferably mixed in a final stage.

In still another catalyst-preparing procedure, as mentioned above, the mixture of the first moiety material and the second moiety material is compression-molded, and the resultant carrier grains are mixed with the catalytic component material.

The catalytic component material can be applied to the carrier by a vapor deposition method, or by stirring a dispersion of the catalytic component material and the carrier material in an inert solvent, or by stirring a mixture of the catalytic component material with the carrier material at a temperature equal to or higher than the melting temperature of the catalytic component material in the absence of a liquid medium.

In the method of the present invention, a dimerization reaction of at least one lower α-olefin monomer is carried out in the presence of the above-mentioned catalyst.

The lower α-olefins usable for the present invention preferably have 2 to 6 carbon atoms, and are more preferably selected from the group consisting of ethylene, propylene, 1-butene, isobutylene, 1-pentene and 1-hexene.

Especially, the catalyst and method of the present invention are advantageously applied to the preparation of 4-methylpentene-1 by the dimerization of propylene, the preparation of 1-pentene by the codimerization of propylene and ethylene, the preparation of 3-methylpentene-1 by the codimerization of 1-butene and ethylene, and the preparation of 2-methylpentene-1 by the codimerization of isobutylene and ethylene. More preferably, the catalyst and method of the present 10 invention are utilized to prepare 4-methylpentene-1 by the dimerization of propylene.

The dimerization and codimerization reaction in accordance with the method of the present invention can be carried out by a gas phase method or a liquid phase method, while heating. Especially, a fixed bed type gas phase reaction system is advantageously used for the method of the present invention.

When the dimerization or codimerization reaction is carried out in a gas phase method, preferably, the reaction temperature is in the range of 50° C. to 250° C., more preferably 80° C. to 200° C. and the reaction pressure is in the range of 20 to 200 kg/cm²G. In the method of the present invention, the α-olefin gas is fed preferably at a liquid hourly space velocity (LHSV) of 0.5 to 10 hr$^{-1}$, more preferably 1 to 7 hr$^{-1}$.

The dimerization or codimerization reaction can be carried out by a batch type system using an autoclave, a vessel type flowing system in which the catalyst and the lower α-olefin feed are continuously fed into an autoclave, or a gas phase, fixed bed system in which a reactor is packed with the catalyst and the lower α-olefin feed flows through the reactor.

The catalyst of the present invention for dimerizing a lower α-olefin monomer or for codimerizing two lower α-olefin monomers is advantageous in that the catalytic activity of the catalyst is retained at a high level over a long period of time, and the aimed dimer is produced at a high selectivity thereto. Especially, where the catalyst and method of the present invention are applied to the dimerization of propylene to produce 4-methylpentene-1, an undesirable isomer, namely 4-methylpentene-2, which is difficult to separate from the aimed dimer, is produced in a reduced yield.

EXAMPLES

The present invention will be further illustrated by the following examples.

In the examples, the conversion of the lower α-olefin monomer, the selectivity of the aimed dimerization product and the conversion rate of the lower α-olefin monomer were determined in accordance with the following equations.

Conversion (%)=A/B×100

A=Total weight (g) of resultant dimerization products

B=Weight (g) of α-olefin monomer feed

Selectivity (%)=C/A×100

C=Weight (g) of resultant aimed dimer

A: As defined above

Conversion rate (g/g–atom metal·hr)=D+(T×M)

D=Weight (g) of converted α-olefin monomer

T=Real reaction time (hr)

M=Amount in gram atom of alkali metal employed for reaction

EXAMPLE 1

A potassium fluoride powder was dried at a temperature of 350° C. for 2 hours, and a graphite powder was dried in a nitrogen atmosphere at a temperature of 650° C. for 2 hours.

The dried potassium fluoride powder (a first moiety) in an amount of 33.95 g was fully mixed with 0.175 g of the dried graphite powder (a second moiety) in a nitrogen gas atmosphere at room temperature. The resultant mixture was mixed with 0.875 g of sodium metal (a catalytic component), and the resultant mixture was heated at a temperature of 350° C. for 2 hours, while stirring.

The composition of the resultant catalyst is shown in Table 1.

From the resultant catalyst, 25.1 g of a sample were taken and placed in a 500 ml autoclave equipped with an electromagnetic stirrer. Into the autoclave, 83 ml of n-heptane were placed and then 83 g of propylene were fed. The autoclave was closed and heated so that the temperature of the reaction system in the autoclave reached 150° C. and maintained at this level for 6.7 hours. It was observed that no pressure reduction of propylene occurred for 1.2 hours after reaching 150° C., and thus the net reaction time (effective reaction time) was 5.5 hours.

After the reaction was completed, the autoclave was cooled to room temperature. Non-reacted propylene was collected by a trap in a dry ice-ethyl alcohol bath, and then the solvent consisting of n-heptane and the reaction product remaining in the autoclave were recovered by a distillation under a reduced pressure.

The collected propylene and the recovered liquid by the reduced pressure distillation were subjected to a gas chromatographic analysis. As a result, the contents of the 4-methylpentene-1 and other olefins having 6 carbon atoms ($C_6$ olefins) in the resultant dimerization reaction product were determined.

The conversion of propylene to the resultant dimers was 32.3%, the selectivity of the resultant dimers to 4-methylpentene-1 was 86.4%, and the conversion rate of propylene was 179 g–$C_3$'/g–atom metal·hr.

Table 2 shows the amount of the catalyst used, the amount of propylene used, the total reaction time, the net reaction time, and the resultant conversion, selectivity and conversion rate.

EXAMPLE 2

The same procedures as in Example 1 were carried out except that the first moiety material consisting of 23.765 g of potassium fluoride and 10.185 g of potassium carbonate was dired at a temperature of 350° C. for 2 hours.

The composition of the catalyst is shown in Table 1 and the reaction conditions and the reaction results are shown in Table 2.

EXAMPLES 3 and 4

In each of Examples 3 and 4, the same procedures as in Example 2 were carried out except that the mixing ratio of the dried potassium fluoride to the potassium carbonate was changed to as shown in Table 1.

The composition of the catalyst is shown in Table 1 and the reaction conditions and the reaction results are shown in Table 2.

EXAMPLES 5 to 7

In each of Examples 5 to 7, the same procedures as in Example 2 were carried out except that potassium chloride was used for potassium carbonate.

The composition of the catalyst is shown in Table 1 and the reaction conditions and the reaction results are shown in Table 2.

Comparative Example 1

The same procedures as in Example 1 were carried out except that potassium fluoride was replaced by potassium carbonate.

Namely no potassium fluoride was employed for the catalyst.

The composition of the catalyst is shown in Table 1 and the reaction conditions and the reaction results are shown in Table 2.

Comparative Example 2

The same procedures as in Example 1 were carried out except that potassium fluoride was replaced by potassium chloride.

Namely, no potassium fluoride was contained in the catalyst.

The composition of the catalyst is shown in Table 1 and the reaction conditions and the reaction results are shown in Table 2.

TABLE 1

| | | | | Item Composition of catalyst | | |
|---|---|---|---|---|---|---|
| Example No. | | Sodium metal (wt %) | Potassium fluoride (wt %) | Another anhydrous potassium compound | | Graphite (wt %) |
| | | | | Type | Amount (wt %) | |
| Example | 1 | 2.5 | 97.0 | — | — | 0.5 |
| | 2 | 2.5 | 67.9 | K$_2$CO$_3$ | 29.1 | 0.5 |
| | 3 | 2.5 | 48.5 | K$_2$CO$_3$ | 48.5 | 0.5 |
| | 4 | 2.5 | 29.1 | K$_2$CO$_3$ | 67.9 | 0.5 |
| | 5 | 2.5 | 67.9 | KCl | 29.1 | 0.5 |
| | 6 | 2.5 | 48.5 | KCl | 48.5 | 0.5 |
| | 7 | 2.5 | 29.1 | KCl | 67.9 | 0.5 |
| Comparative Example | 1 | 2.5 | — | K$_2$CO$_3$ | 97.0 | 0.5 |
| | 2 | 2.5 | — | KCl | 97.0 | 0.5 |

TABLE 2

| | | | | Item | | | | |
|---|---|---|---|---|---|---|---|---|
| Example No. | | Amount (g) | | Reaction time (hr) | | Conversion (%) | Selectivity (%) | Conversion rate g-C$_3$'/ g-at.met.hr |
| | | Catalyst | Propylene | Total | Net | | | |
| Example | 1 | 25.1 | 83 | 6.7 | 5.5 | 32.3 | 86.4 | 179 |
| | 2 | 25.2 | 87 | 7.1 | 5.7 | 30.9 | 86.8 | 172 |
| | 3 | 25.1 | 89 | 6.8 | 6.0 | 31.6 | 86.0 | 172 |
| | 4 | 25.0 | 82 | 6.5 | 5.4 | 36.3 | 87.5 | 203 |
| | 5 | 25.0 | 85 | 7.2 | 6.2 | 34.9 | 85.4 | 176 |
| | 6 | 25.1 | 84 | 7.0 | 6.2 | 33.3 | 88.0 | 165 |
| | 7 | 25.1 | 83 | 7.5 | 6.7 | 34.8 | 84.6 | 158 |
| Comparative Example | 1 | 25.1 | 88 | 8.3 | 7.9 | 28.0 | 86.0 | 114 |
| | 2 | 25.1 | 87 | 7.1 | 0.0 | 0.0 | — | 0 |

EXAMPLE 8

A first moiety material was prepared by mixing 50 parts by weight of an anhydrous potassium fluoride powder having an average particle size of 270 μm, a sparse packing bulk density of 1.148 g/ml, and a specific surface area of 0.09 m$^2$/g determined by the BET method, with 50 parts by weight of an anhydrous potassium carbonate powder having an average particle size of 250 μm, a bulk density of 0.953 g/ml and a specific surface area of 0.84 m$^2$/g. The mixture was crushed to provide a mixture having a bulk density of 0.908 g/ml.

The mixture was further mixed with a graphite powder in an amount of 0.99% by weight based on the total weight of the potassium compound and graphite. The resultant mixture was fully stirred and then compression molded to provide carrier grains in the form of a circular cylinder having a diameter of 3 mm and a height of 3 mm.

The compression molded carrier grains had a crushing strength (in radius direction of the circular cylinder-shaped grain) of 4.2 kg measured by a KIYA-Type hardness tester. After drying at a temperature of 100° C. for 22 hours under a reduced pressure, the dried carrier grains had a specific surface area of 0.54 m$^2$/g.

The dried carrier grains were mixed with 2.50% by weight of sodium metal based on the total weight of the catalyst, in a nitrogen gas atmosphere. The mixture was stirred at a temperature of 370° C. for 4 hours to prepare catalyst grains. The carrier grains exhibited a high absorbing property to the sodium metal, and thus the resultant catalyst grains exhibited a dry touch and do not adhere to each other.

The catalyst grains in an amount of 66.98 g were packed in a catalyst containing portion having a volume of 54 ml, of a tubular reactor having an inside diameter of 21 mm. To the reactor, propylene was continuously fed at a liquid hourly space velocity of 5.1 hr$^{-1}$ while maintaining the reaction pressure at a level of 100 kg/cm$^2$G and the reaction temperature at a level of 150° C., to carried out a continuous flowing type reaction procedure.

The conversion of propylene was 15.4%, the selectivity to 4-methylpentene-1 was 93.8%.

The carrier and catalyst-preparation conditions are shown in Table 3.

The properties of the catalyst and the reaction results are shown in Table 4.

The composition of the resultant reaction product is shown in Table 5.

EXAMPLE 9

The same procedures as in Example 8 were carried out with the following exceptions.

An anhydrous potassium fluoride powder having an average particle size of 280 μm, a bulk density of 1.198 g/ml and a specific surface area of 0.07 m$^2$/g (the 10 BET method) and in an amount of 50 parts by weight was mixed with 50 parts by weight of the same potassium carbonate powder as mentioned in Example 8, and the mixture was crushed. The crushed mixture had a bulk density of 0.893 g/ml and was employed to prepare the compression-molded carrier grains as shown in Table 3.

The resultant carrier grains were dried under the conditions as shown in Table 3, and sodium metal in the amount as shown in Table 4 was carried on the carrier grains. The resultant catalyst grains were subjected to the dimerization procedure under the conditions as shown in Table 4.

The catalyst-containing portion of the reactor had a space of 54 ml and could contain 61.24 g of the catalyst grains.

The preparation conditions of the carrier and catalyst are shown in Table 3, the properties of the catalyst and the reaction results are shown in Table 4, and the composition of the resultant reaction product is shown in Table 5.

EXAMPLE 10

The same procedures as in Example 8 were carried out with the following exceptions.

An anhydrous potassium fluoride powder having an average particle size of 240 µm, a bulk density of 1.253 g/ml, and a specific surface area (the BET method) of 0.11 $m^2/g$ was crushed. The crushed potassium fluoride powder in an amount of 50 parts by weight was mixed with 50 parts by weight of the same potassium carbonate powder as mentioned in Example 8. The resultant mixture had a bulk density of 1.036 g/ml. The mixture was employed to prepare the compression-molded carrier grains as shown in Table 3.

The resultant carrier grains were dried and calcined under the conditions as shown in Table 3, and sodium metal in the amount as shown in Table 4 was carried on the carrier grains. The resultant catalyst grains were subjected to the dimerization procedure under the conditions as shown in Table 4.

The preparation conditions of the carrier and catalyst are shown in Table 3, the properties of the catalyst and the reaction results are shown in Table 4, and the composition of the resultant reaction product is shown in Table 5.

EXAMPLE 11

The same procedures as in Example 8 were carried out with the following exceptions.

A potassium fluoride powder having a bulk density of 0.401 g/ml and a specific surface area (the BET method) of 0.56 $m^2/g$ was wetted with water and granulated. The granulated potassium fluoride was dried at a temperature of 100° C. under a reduced pressure for 20 hours. The dried potassium fluoride particles in an amount of 50 parts by weight were mixed with 50 parts by weight of the same potassium carbonate powder. The resultant mixture had a bulk density of 0.961 g/ml. The mixture was used to prepare the compression-molded carrier grains as shown in Table 3.

The resultant carrier grains were dried under the conditions as shown in Table 3, and sodium metal in the amount as shown in Table 4 was carried on the carrier grains. The resultant catalyst grains were subjected to the dimerization procedure under the conditions as shown in Table 4.

Before the dimerization procedure, the catalyst was analyzed in the following manner.

A sample of the catalyst grains was mixed with butyl cellosolve (2-butoxyethanol) and then with water in a nitrogen gas atmosphere, and a hydrogen gas generated from the reaction mixture was collected into a gas burette. The amount of the collected hydrogen gas was equal to that calculated from the amount of the sodium metal carried on the catalyst.

It was confirmed that in view of a $^{23}Na$ solid NMR spectrum (standard: 3M NaCl aqueous solution), no peak was found at about 1133 ppm which was derived from sodium metal. Certain peaks were found at about 0 ppm which were derived from sodium ions.

The preparation conditions of the carrier and catalyst are shown in Table 3, the properties of the catalyst and the reaction results are shown in Table 4, and the composition of the resultant reaction product is shown in Table 5.

EXAMPLE 12

The same procedures as in Example 8 were carried out with the following exceptions.

The same potassium fluoride powder as that as described in Example 11 in an amount of 20 parts by weight was not granulated and was mixed to 80 parts by weight of the same potassium carbonate as in Example 8. The resultant mixture exhibited a bulk density of 0.769 g/ml.

The mixture was used to prepare the carrier grains as shown in Table 3 in the same manner as in Example 8.

The resultant carrier grains were calcined under the conditions as shown in Table 3, and sodium metal in the amount as shown in Table 4 was carried on the carrier grains. The resultant catalyst grains were subjected to the dimerization procedure under the conditions as shown in Table 4.

The preparation conditions of the carrier and catalyst are shown in Table 3, the properties of the catalyst and the reaction results are shown in Table 4, and the composition of the resultant reaction product is shown in Table 5.

EXAMPLE 13

The same procedures as in Example 8 were carried out with the following exceptions.

A mixture was prepared from the same potassium fluoride and potassium carbonate powders as mentioned in Example 10 in a mixing weight ratio of 30:70. The resultant mixed powder had a bulk density of 1.021 g/ml.

The mixed powder was used to prepare the carrier grains as shown in Table 3 in the same manner as in Example 8.

The resultant carrier grains were calcined under the conditions as shown in Table 3, and sodium metal in the amount as shown in Table 4 was carried on the carrier grains. The resultant catalyst grains were subjected to the dimerization procedure under the conditions as shown in Table 4.

The preparation conditions of the carrier and catalyst are shown in Table 3, the properties of the catalyst and the reaction results are shown in Table 4, and the composition of the resultant reaction product is shown in Table 5.

EXAMPLE 14

The same procedures as in Example 8 were carried out with the following exceptions.

A mixture was prepared from the same potassium fluoride and potassium carbonate powders as in Example 10 in a mixing weight ratio of 60:40. The resultant mixed powder had a bulk density of 1.030 g/ml.

The mixture powder was used to prepare the carrier grains as indicated in Table 3 in the same manner as in Example 8.

The resultant carrier grains were dried under the conditions as shown in Table 3, sodium metal in the amount as shown in Table 4 was carried on the carrier grains. The resultant catalyst grains were subjected to the dimerization procedure under the conditions as shown in Table 4.

The preparation conditions of the carrier and catalyst are shown in Table 3, the properties of the catalyst and the reaction results are shown in Table 4, and the composition of the resultant reaction product is shown in Table 5.

Comparative Examples 3 and 4

In each of Comparative Examples 3 and 4, the same procedures as in Example 8 were carried out with the following exceptions.

No potassium fluoride was used. Therefore, the first moiety material consisted of a non-crushed potassium carbonate powder.

Before the resultant catalyst was employed for the dimerization reaction of propylene, a sample of the catalyst grains was subjected to the same analysis as in Example 11.

The amount of hydrogen gas generated from the catalyst sample was equal to that calculated from the amount of the sodium metal contained in the catalyst.

In the $^{23}$Na solid NMR spectrum (3M NaCl aqueous solution standard), no peak was found at about 1133 ppm which corresponded to sodium metal, and certain peaks at about 0 ppm corresponding to sodium ions were found.

The preparation conditions of the carrier and catalyst are shown in Table 3, the properties of the catalyst and the reaction results are shown in Table 4, and the composition of the resultant reaction product is shown in Table 5.

Comparative Examples 5 and 6

The same procedures as in Comparative Example 3 were carried out with the following exceptions.

The amount of the graphite was as shown in Table 3, and the carrier grains exhibited the crushing strength as shown in Table 3.

The preparation conditions of the carrier and catalyst are shown in Table 3, the properties of the catalyst and the reaction results are shown in Table 4, and the composition of the resultant reaction product is shown in Table 5.

TABLE 3

| | | | | | | | | | | |
|---|---|---|---|---|---|---|---|---|---|---|
| | | | | | | Item | | | | |
| | | | | | | Carrier | | | | |
| | | Mixing | Content | | Drying conditions | | | Calcining conditions | | Specific |
| Example No. | | weight ratio KF/K$_2$CO$_3$ | of graphite (wt %) | Crushing strength (kg) | Temperature (°C.) | Pressure | Time (hr) | Temperature (°C.) | Time (hr) | surface area (m$^2$/g) |
| Example | 8 | 50/50 | 0.99 | 4.2 | 100 | Reduced | 22 | — | — | 0.54 |
| | 9 | 50/50 | 0.99 | 5.1 | 100 | Reduced | 19 | — | — | 0.32 |
| | 10 | 50/50 | 0.99 | 4.8 | 100 | Reduced | 23 | 380 | 2 | 0.31 |
| | 11 | 50/50 | 0.99 | 5.2 | 100 | Reduced | 17 | — | — | 0.42 |
| | 12 | 20/80 | 0.99 | 5.7 | — | — | — | 380 | 2 | 0.33 |
| | 13 | 30/70 | 1.96 | 4.5 | — | — | — | 380 | 2 | 0.44 |
| | 14 | 60/40 | 0.99 | 4.9 | 100 | Reduced | 26 | — | — | 0.57 |
| Comparative Example | 3 | 0/100 | 0.99 | 4.9 | — | — | — | 380 | 2 | 0.70 |
| | 4 | 0/100 | 0.99 | 6.7 | 100 | Reduced | 24 | 380 | 2 | 0.74 |
| | 5 | 0/100 | 1.48 | 4.7 | — | — | — | 380 | 2 | 0.60 |
| | 6 | 0/100 | 1.96 | 4.3 | — | — | — | 380 | 2 | 0.74 |

TABLE 4

| | | | Item | | | | |
|---|---|---|---|---|---|---|---|
| | | | Catalyst | | | | |
| | | | Amount of | | | Reaction | |
| Example No. | | Content of Na (wt %) | catalyst packed (g) | Crushing strength (kg) | LHSV (hr$^{-1}$) | Conversion (%) | Selectivity (%) |
| Example | 8 | 2.50 | 66.98 | 4.4 | 5.1 | 15.4 | 93.8 |
| | 9 | 2.50 | 61.24 | 5.0 | 5.0 | 11.7 | 93.3 |
| | 10 | 2.51 | 66.45 | 5.4 | 5.3 | 15.8 | 93.1 |
| | 11 | 2.50 | 66.28 | 6.7 | 5.0 | 11.6 | 93.8 |
| | 12 | 2.51 | 63.15 | 4.8 | 4.9 | 11.3 | 93.2 |
| | 13 | 2.51 | 58.64 | 4.5 | 5.2 | 14.1 | 93.2 |
| | 14 | 2.50 | 66.38 | 4.6 | 4.9 | 13.0 | 93.4 |
| Comparative Example | 3 | 2.48 | 61.63 | 7.5 | 5.3 | 14.3 | 92.1 |
| | 4 | 2.52 | 65.69 | 5.7 | 4.9 | 12.2 | 89.9 |
| | 5 | 2.48 | 58.17 | 6.2 | 5.0 | 12.5 | 92.5 |
| | 6 | 2.49 | 62.47 | 5.5 | 5.1 | 11.6 | 92.4 |

TABLE 5

| Example No. | | (A) 4-methyl-pentene-1 (wt %) | (B) 4-methyl-pentene-2 (wt %) | Ratio (A)/((A) + (B)) (%) |
|---|---|---|---|---|
| Example | 8 | 93.8 | 1.0 | 98.9 |
| | 9 | 93.3 | 0.9 | 99.0 |
| | 10 | 93.1 | 1.4 | 98.5 |
| | 11 | 93.8 | 1.4 | 98.5 |
| | 12 | 93.2 | 1.4 | 98.5 |
| | 13 | 93.2 | 1.3 | 98.6 |
| | 14 | 93.4 | 1.4 | 98.5 |
| Comparative Example | 3 | 92.1 | 2.0 | 97.9 |
| | 4 | 89.9 | 4.2 | 95.5 |
| | 5 | 92.5 | 1.6 | 98.3 |
| | 6 | 92.4 | 1.4 | 98.5 |

We claim:

1. A catalyst for dimerizing at least one lower alpha-olefin monomer, comprising a carrier comprising a mixture of a first moiety which comprises anhydrous potassium fluoride, with anhydrous potassium carbonate with a second moiety which comprises at least one carbon material; and a catalytic component carried on the carrier and comprising at least one alkali metal.

2. The catalyst as claimed in claim 1, wherein the carrier is in the form of compression-molded grains.

3. The catalyst as claimed in claim 2, wherein the compression-molded carrier grains have a specific surface area of 0.25 m²/g or more.

4. The catalyst as claimed in claim 1, wherein the second moiety of the carrier comprises at least one member selected from the group consisting of activated carbon, graphite and carbon black.

5. The catalyst as claimed in claim 1, wherein the second moiety of the carrier is present in an amount of 0.2 to 3.0% based on the total weight of the carrier.

6. The catalyst as claimed in claim 1, wherein the catalytic component is present in an amount of 1 to 10% based on the total weight of the catalyst.

7. The catalyst as claimed in claim 1, wherein the alkali metal for the catalytic component is selected from the group consisting of sodium and potassium metals.

8. The catalyst as claimed in claim 2, wherein the compression-molded carrier grains have a size of from 0.5 to 10 mm.

9. The catalyst as claimed in claim 1 wherein in the first moiety of the carrier, the anhydrous potassium fluoride and the anhydrous potassium carbonate, are present in a weight ratio of 10:90 to 80:20.

* * * * *